United States Patent [19]
Schoenfeld

[11] Patent Number: 5,217,444
[45] Date of Patent: Jun. 8, 1993

[54] ABSORBENT TAMPON

[76] Inventor: Alex Schoenfeld, 50 Ibn Gvirol St., Tel Aviv, Israel

[21] Appl. No.: 369,805

[22] Filed: Jun. 22, 1989

[30] Foreign Application Priority Data

Nov. 11, 1987 [IL] Israel ........................................ 84443

[51] Int. Cl.$^5$ ............................................ A61F 13/15
[52] U.S. Cl. ................................... 604/361; 604/358; 604/385.1
[58] Field of Search ............... 604/358, 360, 361, 318, 604/385.1

[56] References Cited

U.S. PATENT DOCUMENTS

| | | | |
|---|---|---|---|
| 4,022,211 | 6/1977 | Timmons et al. | 604/361 |
| 4,231,370 | 11/1980 | Mroz et al. | 604/361 |

FOREIGN PATENT DOCUMENTS

| | | | |
|---|---|---|---|
| 2031104 | 6/1970 | Fed. Rep. of Germany | 604/361 |
| 1355018 | 2/1964 | France | 604/361 |
| 3320218 | 12/1984 | France | 604/358 |

OTHER PUBLICATIONS

W. J. Watson, MD, CCFP, Gregory DeMarchi, MD, CCFP, pp. 1847-1852 Vaginal Discharge: An Approach to Diagnosis and Management, Aug., 1987.

Primary Examiner—Randall L. Green
Assistant Examiner—Gina M. Gualtieri
Attorney, Agent, or Firm—Benjamin J. Barish

[57] ABSTRACT

An absorbent pad, for use in absorbing secretions from a person's body, includes a pH indicator material indicating by a colour change the acidity or alkalinity of a liquid coming into contact with it. The pH indicator material is wetted by the secretions absorbed by the pad, and thereby provides an indication of the health condition of the person's body.

4 Claims, 1 Drawing Sheet

ABSORBENT TAMPON

BACKGROUND OF THE INVENTION

The present invention relates to an absorbent pad, and particularly to one for use in absorbing secretions from a person's body. The invention is particularly useful in tampons, namely plugs of absorbent material insertable into body cavities to absorb secretions, particularly vaginal discharge, and is therefore described below with respect to this application.

Vaginal discharge caused by secretions from the cervix and vagina may occur throughout the menstrual cycle. Such discharge may result from both non-infectious causes and infectious causes. The non-infectious causes include physiological causes, such as puberty, menstrual cycle, sexual activity, pregnancy and menopause, as well as non-physiological causes such as the presence of a foreign body, chemical, drug, and gynecologic abnormalities. The infectious causes producing vaginal secretions include Candida albicans, Trichimonas vaginalis, and Bacterial vaginosis; and those producing cervical secretions include Neisserria gonorrhea, Chlamydia tracomatis and Herpes simplex virus. Effective treatment requires identification of the cause of the secretion, particularly if the cause is an infectious one.

At the present time, diagnosis of the cause of a vaginal or cervical secretion is usually made at the physician's office or in a laboratory by examining smears of the discharge. One of such examinations made is to measure the pH, i.e., the acidity or alkalidity, of the secretion since it has been determined that at least some of the infectious causes are characterized by a change in the pH of the secretion. For further information, reference is made to the publication "Vaginal Discharge: An Approach to Diagnosis and Management", by William J. Watson and Gregory DeMarchi, Can. Fam. Physician, Vol. 33 August 1987, Pages 1847-1855.

OBJECTS AND SUMMARY OF THE INVENTION

An object of the present invention is to provide a method and means which can be conveniently examined by the user to provide an early indication of the health condition of the user's body, particularly whether there may be an infectious cause for a vaginal discharge.

According to the present invention, there is provided a tampon for use in absorbing secretions from a person's body, particularly vaginal discharge, characterized in that the tampon includes a pH indicator material indicating by a colour change the acidity or alkalinity of the secretion coming into contact with the material, the pH indicator material being included in the tampon so as to be wetted by the secretions absorbed by the tampon, thereby providing an indication of the health condition of the person's body.

The invention also provides a method for indicating the health condition of a woman, comprising: including in a tampon to be used for absorbing vaginal discharge a pH indicator material indicating by a colour change the acidity or alkalinity of the vaginal discharge; and inspecting the colour of the pH indicator material after being used for absorbing vaginal discharge.

Preferably, the tampon includes a plurality of pH indicator materials each producing a colour change at a different pH value, to provide a more precise indication of the specific pH value, to provide a more precise indication of the specific pH value of the secretion absorbed by the tampon, and thereby a better indication of the health condition of the user.

The pH indicator material may be impregnated in a fibrous strip bonded to the tampon such as to be wetted by the secretions of the person's body absorbed by the tampon; alternatively, the pH indicator material may be impregnated in at least a portion of the tampon such as to be wetted by the secretions of the person's body absorbed by the tampon.

The users of such tampons would be instructed to visually inspect the colour of the tampon, or the portion thereof carrying the pH indicator material, and if a certain colour change occurred, to immediately seek an examination by the user's physician in order to make the further tests required in order to diagnose the cause of the secretion, and particularly whether it is an infectious cause. For example, a normal vaginal discharge has a pH of less than 4.5, whereas a pH of greater than 5.0 indicates the possibility of the presence of Trichimonas vaginalis or Bacterial vaginosis. Therefore, if the pH indicator material applied to the tampon produced a colour change between pH 4.5 and 5.0, this indicates the possibility of one of these infections. The user could visually inspect the colour of the tampon after its use and if such a colour change occured, indicating the possibility of one of these infectious causes for the vaginal discharge, she would be immediately alerted to see her physician to enable further tests to be performed so as to determine the precise reason for the discharge.

BRIEF DESCRIPTION OF THE DRAWINGS

The invention is herein described, somewhat diagrammatically and by way of example only, with reference to the accompanying drawings, wherein.

DESCRIPTION OF PREFERRED EMBODIMENTS

Figure 1:
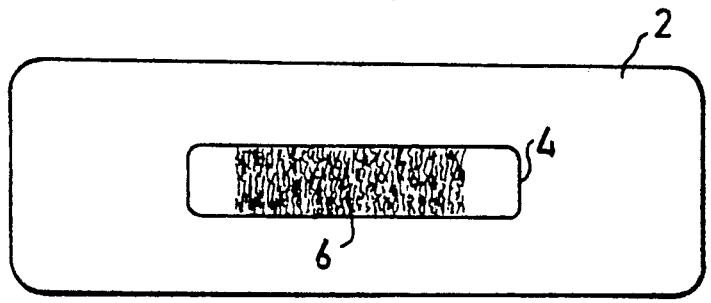
FIG. 1 illustrates a tampon including a fibrous strip of filter paper bonded to it and impregnated with a pH indicator material.

Colour-change pH indicator materials are well-known providing an indication for almost any pH determination that may be needed. The attached table lists commercially-available pH indicator materials covering substantially the complete pH range.

| PH INDICATOR MATERIALS | | | | |
|---|---|---|---|---|
| pH Indicators | Colour | pH Transition Intervals | | Colour |
| Cresol red | pink | 0.2 | 1.8 | yellow |
| m-Cresol purple | red | 1.2 | 2.8 | yellow |
| Thymol blue | red | 1.2 | 2.8 | yellow |
| p-Xylenol blue | red | 1.2 | 2.8 | yellow |
| 2,2',2'',4,4'-Pentamethoxy-triphenylcarbinol | red | 1.2 | 3.2 | colourless |
| 2,4-Dinitrophenol | colourless | 2.8 | 4.7 | yellow |
| 4-Dimethylaminoazobenzene | red | 2.9 | 4.0 | yellow-orange |
| Bromochlorophenol blue | yellow | 3.0 | 4.6 | purple |
| Bromophenol blue | yellow | 3.0 | 4.6 | purple |

-continued

PH INDICATOR MATERIALS

| pH Indicators | Colour | pH Transition Intervals | | Colour |
|---|---|---|---|---|
| Methyl orange | red | 3.1 | 4.4 | yellow-orange |
| Bromocresol green | yellow | 3.8 | 5.4 | blue |
| 2,5-Dinitrophenol | colourless | 4.0 | 5.8 | yellow |
| Alizarinsulfonic acid sodium salt | yellow | 4.3 | 6.3 | violet |
| Methyl red | red | 4.4 | 6.2 | yellow-orange |
| Methyl red sodium salt | red | 4.4 | 6.2 | yellow-orange |
| Chlorophenol red | yellow | 4.8 | 6.4 | purple |
| Hematoxylin | yellow | 5.0 | 7.2 | violet |
| Litmus extra pure | red | 5.0 | 8.0 | blue |
| Bromophenol red | orange-yellow | 5.2 | 6.8 | purple |
| Bromocresol purple | yellow | 5.2 | 6.8 | purple |
| 4-Nitrophenol | colourless | 5.4 | 7.5 | yellow |
| Bromoxylenol blue | yellow | 5.7 | 7.4 | blue |
| Alizarin | yellow | 5.8 | 7.2 | red |
| Bromothymol blue | yellow | 6.0 | 7.6 | blue |
| Phenol red | yellow | 6.4 | 8.2 | red |
| 3-Nitrophenol | colourless | 6.6 | 8.6 | yellow-orange |
| Neutral red | bluish-red | 6.8 | 8.0 | orange-yellow |
| 4,5,6,7-Tetrabromophenol-phthalein | colourless | 7.0 | 8.0 | purple |
| Cresol red | orange | 7.0 | 8.8 | purple |
| 1-Naphtholphthalein | brownish | 7.1 | 8.3 | blue-green |
| m-Cresol purple | yellow | 7.4 | 9.0 | purple |
| Thymol blue | yellow | 8.0 | 9.6 | blue |
| p-Xylenol blue | yellow | 8.0 | 9.6 | blue |
| Phenolphthalein | colourless | 8.2 | 9.8 | red-violet |
| Thymolphthalein | colourless | 9.3 | 10.5 | blue |
| Alizarin yellow GG | light | 10.2 | 12.1 | brownish-yellow |
| Epsilon blue | orange | 11.6 | 13.0 | violet |

Where the absorbent pad is in the form of a tampon for absorbing vaginal discharge, it is preferable that the pH indicator material be one of those in the above list changing its colour between a pH of 4.5 and a pH of 5.0. This would thereby provide an indication of the possibility of the presence of Trichimoniasis or Bacterial vaginosis if the vaginal discharge produced a colour change showing a pH of greater than 5.0.

Preferably, the pH indicator material is impregnated in a fibrous strip of filter paper and bonded, as by an adhesive, to the absorbent pad such as to be wetted by the secretions of the person's body absorbed by the pad. Indicator papers providing a substantially complete range of pH values are commercially available, as indicated by the above table. It is also contemplated that two or more such indicator papers, for different pH values, could be applied to the absorbent pad, and thereby to provide a more precise indication of the specific pH value of the secretion absorbed by the pad, and thereby a better indication of the cause for such secretion.

Alternatively, the pH indicator material may be impregnated in at least a portion of the absorbent pad such as to be wetted by the secretions. It is contemplated here also that the absorbent pad may be impregnated with two or more different pH indicator materials, e.g., along different striped portions thereof, to provide a more precise indication of the actual pH of the secretion.

Figure 2:
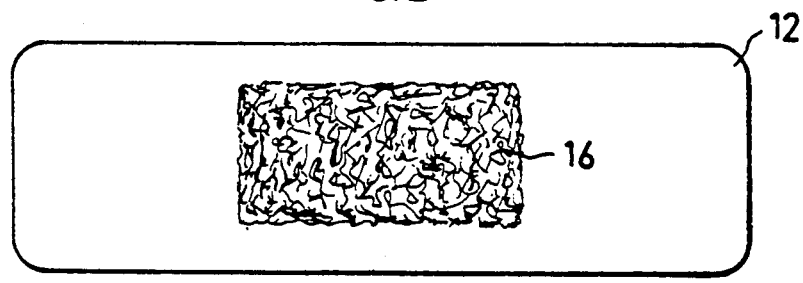
FIG. 2 illustrates a tampon directly impregnated with the pH indicator material.
Figure 3:
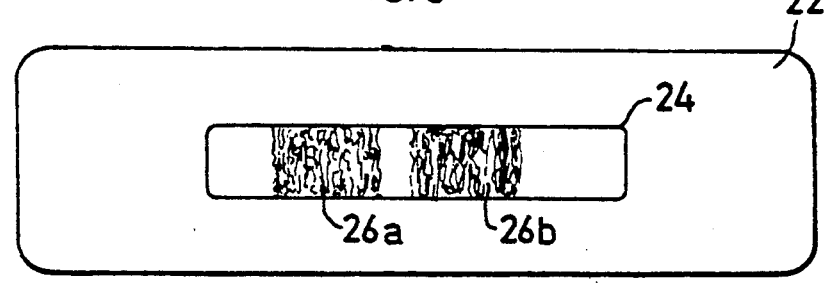
FIG. 3 illustrates a tampon carrying two indicator papers impregnated with a pH indicator material of different pH values.

The foregoing structures are illustrated in the drawings. Thus, FIG. 1 illustrates a tampon 2 including a fibrous strip of filter paper 4 bonded to the tampon and impregnated with a pH indicator material 6; FIG. 2 illustrates a tampon 12 directly impregnated with the pH indicator material 16; and FIG. 3 illustrates a tampon 22 including a fibrous strip 24 carrying two (or more) indicator papers 26a, 26b impregnated with a pH indicator material or different pH values.

While the invention has been described with respect to an absorbent pad in the form of a tampon for absorbing vaginal discharges and for providing an indication of the possibility of an infectious cause of the vaginal discharge, it will be appreciated that the invention could be applied to other forms of absorbent pads for absorbing other body secretions in order to provide an indication of the pH of the body secretion, and thereby an indication of the health condition of the person's body.

What is claimed is:

1. A tampon for absorbing vaginal discharge, characterized in that the tampon includes two pH indicator materials of different pH values indicating by a colour change the acidity or alkalinity of a liquid coming into contact with said materials, said pH indicator materials being included in the tampon so as to be wetted by the secretions absorbed by the tampon, thereby providing an indication of the health condition of the person's body.

2. The tampon according to claim 1, wherein said pH indicator materials are impregnated in a fibrous strip bonded to the tampon such as to be wetted by the secretions of the person's body absorbed by the tampon.

3. The tampon according to claim 2, wherein said pH indicator materials are impregnated in at least a portion of the tampon such as to be wetted by the secretions of the person's body absorbed by the tampon.

4. The tampon according to claim 2, wherein each of said pH indicator materials produces a colour change at a pH of between 4.5 and 5.0.

* * * * *